(12) United States Patent
Azevedo

(10) Patent No.: US 11,878,111 B2
(45) Date of Patent: Jan. 23, 2024

(54) VENTURI INHALATION DEVICE

(71) Applicant: Max Azevedo, Lenoir, NC (US)

(72) Inventor: Max Azevedo, Lenoir, NC (US)

( * ) Notice: Subject to any disclaimer, the term of this patent is extended or adjusted under 35 U.S.C. 154(b) by 57 days.

(21) Appl. No.: 17/356,830

(22) Filed: Jun. 24, 2021

(65) Prior Publication Data

US 2021/0402112 A1    Dec. 30, 2021

Related U.S. Application Data

(60) Provisional application No. 63/043,315, filed on Jun. 24, 2020.

(51) Int. Cl.
*A61M 15/00* (2006.01)

(52) U.S. Cl.
CPC .... *A61M 15/0036* (2014.02); *A61M 15/0021* (2014.02)

(58) Field of Classification Search
CPC ... A61M 15/0033–0036; A61M 15/004–0041; A61M 15/0021; A61M 11/06; A61M 15/0025; A61M 2202/0468; A61M 2205/7509; A61M 2205/7518; A61M 2205/7545; B05B 7/00; B05B 7/0012
USPC .................................................. 128/200.24
See application file for complete search history.

(56) References Cited

U.S. PATENT DOCUMENTS

| | | | |
|---|---|---|---|
| 1,021,688 A | 3/1912 | Jeune | |
| 1,296,128 A | 3/1919 | Siebrandt | |
| 1,374,115 A | 4/1921 | Roemer | |
| 3,153,411 A | 10/1964 | Unks | |
| 3,385,292 A | 5/1968 | Hardy | |
| 5,201,308 A * | 4/1993 | Newhouse | A61M 15/0016 128/203.15 |
| 5,478,307 A | 12/1995 | Wang | |
| 5,820,532 A | 10/1998 | Oliver | |
| 6,007,507 A | 12/1999 | Ledany | |
| 9,173,649 B2 | 11/2015 | Clark et al. | |
| 2011/0088690 A1* | 4/2011 | Djupesland | A61M 15/009 128/203.18 |
| 2020/0261665 A1 | 8/2020 | Pell et al. | |

FOREIGN PATENT DOCUMENTS

| | | | | |
|---|---|---|---|---|
| WO | WO-9640441 A1 * | 12/1996 | ........ | A61M 15/0045 |
| WO | WO-2020254668 A1 * | 12/2020 | ............. | A24F 40/10 |

* cited by examiner

*Primary Examiner* — Elliot S Ruddie
(74) *Attorney, Agent, or Firm* — Boudwin Intellectual Property Law, LLC; Daniel Boudwin

(57) ABSTRACT

A venturi inhalation device is provided. The device has a tube defining an internal volume with a fine bore needle disposed at one end. The fine bore needle is in fluid communication with the internal volume of the tube such that medication stored therein can pass into the needle. The tube has a second end which can be sealed to contain the medication until the device is used. A hollow housing is sized and shaped to receive the tube in close tolerance, whereupon the tube being so received, an air-tight seal is formed. The housing also includes a venturi restriction, and when the tube is received by the first end of the housing, a distal end of the fine bore needle is placed within the venturi restriction. A mouthpiece is disposed on a second end of the housing enabling a user to inhale the medication in the tube.

3 Claims, 2 Drawing Sheets

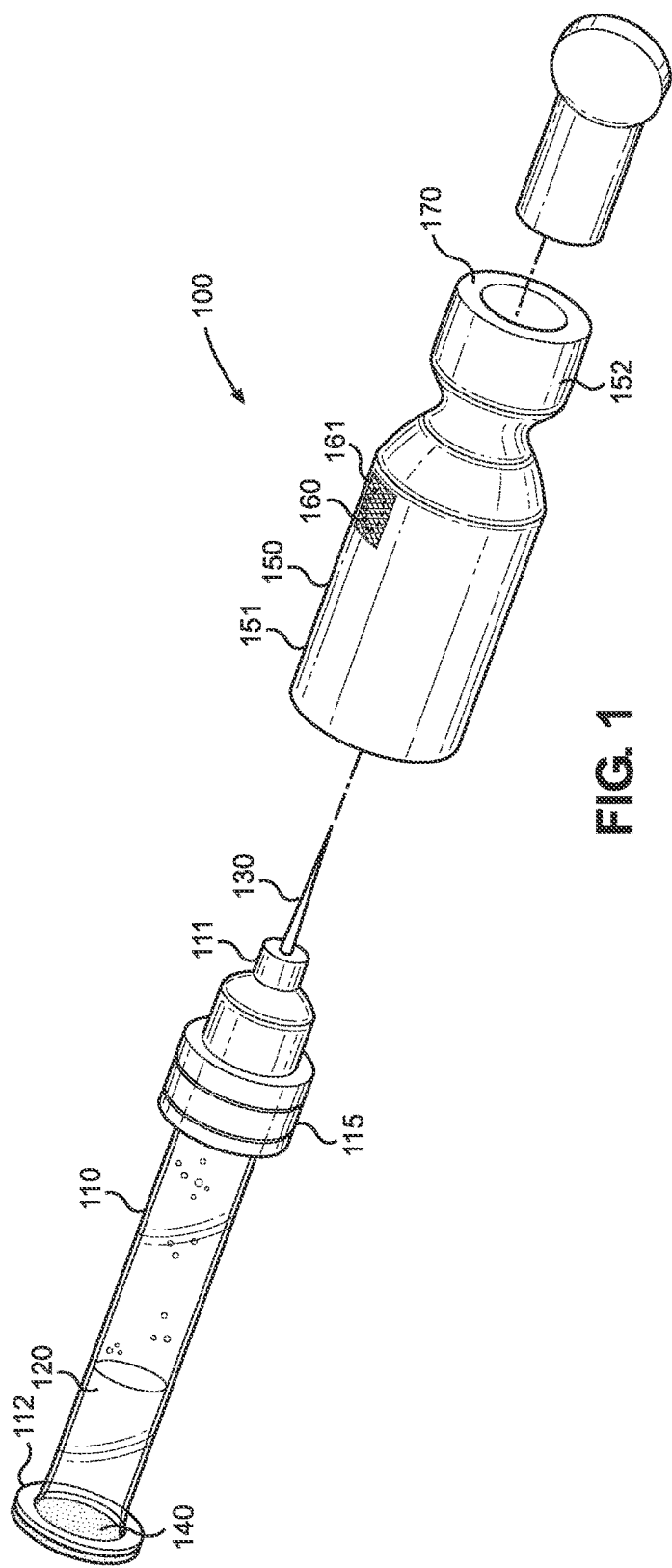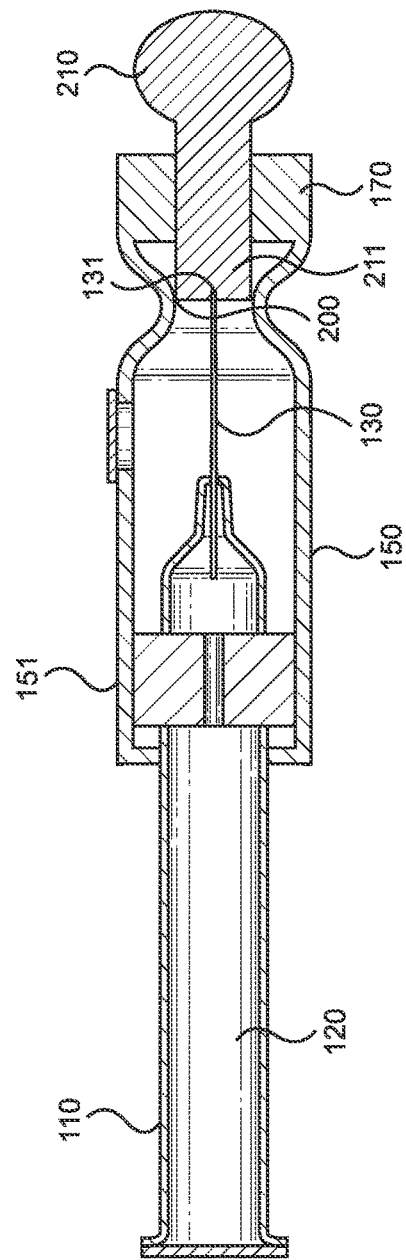

VENTURI INHALATION DEVICE

CROSS REFERENCE TO RELATED APPLICATIONS

Figure 3A:
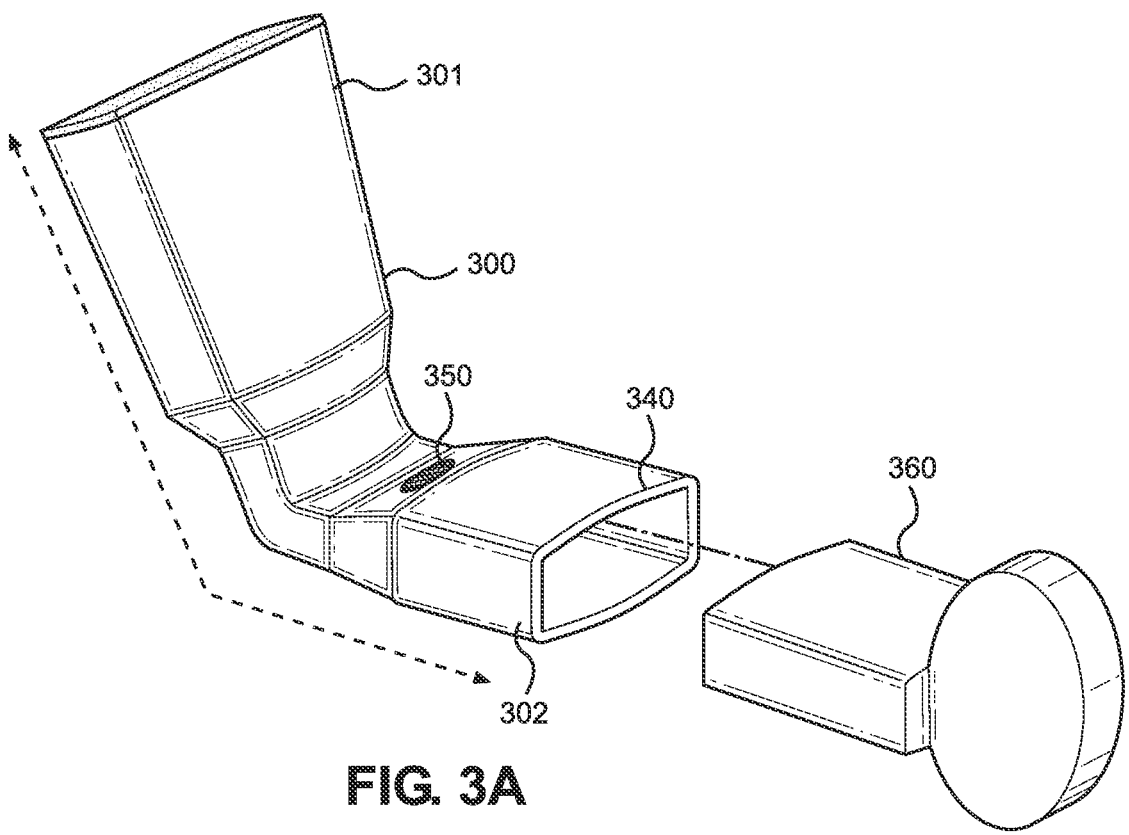

This application claims the benefit of U.S. Provisional Application No. 63/043,315 filed on Jun. 24, 2020. The above identified patent application is herein incorporated by reference in its entirety to provide continuity of disclosure.

BACKGROUND OF THE INVENTION

The present invention relates to medication delivery devices. More particularly, the present invention provides for an inhalation device that can be used with a large variety of medications to directly administer said medication to the lungs, thereby preventing the need for injection or other more harmful forms of administration. Such pharmaceutical dosing via inhalation provides a direct delivery of drugs into the circulatory system resulting in rapid uptake and universality of permissible medications.

Many people utilize injections to administer drugs and medications directly into a patient's blood system in order to treat bacterial or viral infections as well as other medical conditions. Other forms of administration include ingestion or suppository use in order to introduce the medication to the patient's system. Presenting medications via these methodologies leads to a tortuous pathway through the digestive system, or similar systems. Such methodologies can have significant lag time to efficacy. The "shotgun" approach taken by these methods delivers the treatment to the entire body, which, in turn, follows transmission across body tissue to reach the attacking microbe or site of treatment. Because the approach taken delivers treatment to the entire body, the concentrations of the medications and drugs much be sufficiently high in order to enable an adequate amount of medication to reach the targeted area.

In some instances, inhalation of medication is offered as an alternate pathway to introduce the desired drug to a patient's system. Respirators and inhalators are well known in the art but rely on depositing the medications on fine particles. These fine particles act as carriers to transport the medication into the lungs and related circulatory pathways. For example, cyanoacrylate polymer microparticles can be used as such a transporter, resulting in the patient inhaling dust, in effect. Such transporters can damage a patient's system and necessitate a larger volume of material needed to be inhaled in order to provide sufficient quantities of the desired medication.

Inhalation devices, such as respirators, tend to heat the desired material in order to vaporize it. Some devices utilize pressure in addition to the application of heat in order to properly aerosolize the desired molecules. There are numerous other ways, such as humidifiers, that are used to generate aerosols by heat or electronically via ultrasonic waves. All of these such inhalant devises deliver nano sized, or comparably sized particles, based on solid materials impregnated with the active pharmaceutical and typically propelled by fluorinated hydrocarbons, or other pressurizing agents. The issue of how much material is desired to be used can vary because of dilution as delivery requires the entire body to be exposed to the substances and the target sees small dosage by the body's dilution.

The present invention provides a medication delivery device that does not depend on heat application, ultrasonic waves, or pressure differentials established by an outside force. The present venturi inhalation device generates atomization in a venturi device by inhalation alone. Specifically, a capillary tube is concentrically positioned at the throat section of the venturi. Thus, the present invention substantially diverges in design elements from the known art and consequently it is clear that there is a need in the art for an improvement to existing medication delivery devices. In this regard the present invention substantially fulfills these needs.

SUMMARY OF THE INVENTION

In view of the foregoing disadvantages inherent in the known types of medication delivery devices now present in the art, the present invention provides an inhalation device that can be used with a large variety of medications to directly administer said medication to the lungs, thereby preventing the need for injection or other more harmful forms of administration. The present venturi inhalation device comprises a tube defining an internal volume with a fine bore needle disposed at one end. The fine bore needle is in fluid communication with the internal volume of the tube such that medication stored therein can pass into the needle. The tube has a second end which can be sealed to contain the medication until the device is used. A hollow housing is sized and shaped to receive the tube in close tolerance, whereupon the tube being so received, an air-tight seal is formed. The housing also includes a venturi restriction, and when the tube is received by the first end of the housing, a distal end of the fine bore needle is placed within the venturi restriction. A mouthpiece is disposed on a second end of the housing enabling a user to inhale the medication in the tube.

Other objects, features, and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 1 shows an exploded view of an embodiment of the venturi inhalation device.

FIG. 2 shows a cross-sectional view of an embodiment of the venturi inhalation device.

FIG. 3A shows a perspective view of an alternate embodiment of the venturi inhalation device.

FIG. 3B shows a cross-sectional view of an alternate embodiment of the venturi inhalation device.

DETAILED DESCRIPTION OF THE INVENTION

Reference is made herein to the attached drawings. Like reference numerals are used throughout the drawings to depict like or similar elements of the venturi inhalation device. For the purposes of presenting a brief and clear description of the present invention, a preferred embodiment will be discussed as used for the venturi inhalation device. The figures are intended for representative purposes only and should not be considered to be limiting in any respect.

Referring now to FIG. 1, there is shown an exploded view of an embodiment of the venturi inhalation device. The venturi inhalation device 100 comprises a tube 110 defining an internal volume 120. In various embodiments, the tube 110 is composed of glass, plastic, or other liquid impermeable materials such that a liquid stored within the internal volume 120 will not leak or seep out. An object of the present invention is to deliver a therapeutic that can be solubilized or otherwise dispersed within a liquid. Thus, the tube 110 is configured to contain the liquid with the therapeutic until a desired administration thereof. In various further embodiments, an exterior surface of the tube 110 comprises measurement indicia such that a user is able to determine an amount of liquid medication in the tube and can administer a desired dosage thereof. In the preferred embodiment, the tube is charged with a predefined dosage.

A fine bore needle 130 is disposed at a first end 111 of the tube 110. The fine bore needle 130 is in fluid communication with the internal volume 120. In this manner, the liquid containing a therapeutic or medication that is stored within the internal volume 120 can be dispensed through the fine bore needle 130 when an outside force, such as a vacuum created by a user's mouth, as further detailed below, is applied to the fine bore needle 130. Various gauges of needles are contemplated by the present disclosure and the tube 110 and fine bore needle 130 can vary depending on the medication dosage required.

The tube 110 further comprises a closed second end 112. In this manner, the liquid stored within the internal volume 120 will not spill out as the tube 110 is manipulated and transported from one place to another. In some embodiments, the closed second end 112 of the tube 110 comprises a laminate layer 140. In further embodiments, the laminate layer 140 is a heat-sealed laminate. In one embodiment, the heat-sealed laminate is an aluminum laminate material disposed over the entirety of the closed second end 112. The laminate layer 140 enables the internal volume 120 of the tube 110 to be quickly and easily filled and then capped off providing an efficiency of creating predefined dosages of a desired therapeutic for mass consumption. In the preferred use, the laminate layer 140 is pricked open in order to enable the liquid stored within the internal volume 120 to flow through the fine bore needle 130.

A hollow housing 150 is sized and shaped to receive the tube 110 in close tolerance. In the shown embodiment, a collar 115 is disposed around a circumference of an exterior of the tube 110 wherein the collar is sized to frictionally engage with an interior surface of the hollow housing 150 thereby enabling a friction fit between the tube 110 and the hollow housing 150. In various further embodiments, rubber or other similar materials can be disposed within the collar 115 to enable an easier and more secure friction fit. In this manner, whereupon the tube 110 being received by a first end 151 of the housing 150, an air-tight seal is formed between the tube 110 and the first end 151 of the housing 150 (as shown in FIG. 2).

In some embodiments, the hollow housing 150 further comprises an air inlet opening 160. The air inlet opening 160 enables air to flow into and outside the hollow housing 150 when appropriate forces are applied thereto, such as by inhalation as further detailed below. In some further embodiments, an air filter 161 is disposed over an external surface of the air inlet opening 160 such that particulate materials in the air are filtered out and are not pulled into the interior of the hollow housing 150. In some further embodiments, the air filter 161 can be configured to filter out smaller particulate matter such as viruses, bacteria, and other contagions.

A mouthpiece 170 is disposed on a second end 152 of the housing 150. An object of the present invention is to enable a user to atomize a formulation by drawing a breath through the present device, thereby creating a pressure differential. This pressure differential is similar to inhalers and atomizers, except that the pressure differential is created solely by the user's lungs and does not require any external forces such as a pump, motor, electricity, or other means. When the tube 110 is secured within the hollow housing 150, the mouthpiece 170 enables the user to inhale the therapeutic stored within the internal volume 120 of the tube 110 by simply drawing in a breath while securing their mouth over the mouthpiece 170.

Referring now to FIG. 2, there is shown a cross-sectional view of an embodiment of the venturi inhalation device. The hollow housing 150 further comprises a venturi restriction 200. In the shown embodiment, the venturi restriction 200 is formed by opposing concave walls in an interior surface of the hollow housing 150. Thus, in the shown embodiment, an interior surface of the hollow housing 150 is contoured to form the venturi restriction 200. Additionally, in the shown embodiment, an exterior surface of the hollow housing 150 mimics the contours of the interior surface in order to minimize materials as well as to provide a grip that a user can utilize when holding the device. The present disclosure also contemplates an exterior surface that does not mimic the internal surface of the hollow housing 150, wherein the interior surface of the hollow housing 150 still forms a venturi restriction 200.

The venturi restriction 200 is a narrow channel through which air can flow. A width of the venturi restriction 200 is less than a width of an interior diameter of the hollow housing 150. In the shown embodiment, when the tube 110 is received by the first end 151 of the hollow housing 150, a distal end 131 of the fine bore needle 130 is positioned in a venturi throat 201, wherein the venturi throat is defined as the space between the venturi restriction 200. In use, when a user inhales utilizing the present device, air is drawn through the venturi restriction 200 and the air expands in proximity of a distal end 131 of the fine bore needle 130. This creates a high air flow around the distal end 131 of the fine bore needle 130 and the air impinges on the liquid stored in the internal volume 120 generating atomized liquid particles that are inhaled by the user without any outside means such as a pump, motor, or other physical or electrical mechanism resulting in assisted propellants.

In the shown embodiment, a plug 210 is removably secured in the mouthpiece 170. In one embodiment, the plug 210 is a silicone elastomeric plug. The plug 210 ensures that fluid stored within the internal volume 120 does not leak out of the device. In one embodiment, when the plug 210 is secured in the mouthpiece 170, an air-tight seal is formed between the plug 210 and the mouthpiece 170 via a friction fit. In the shown embodiment, when the plug 210 is secured in the mouthpiece 170, the distal end 131 of the fine bore needle 130 penetrates a first end 211 of the plug 210. In this manner, the plug 210 ensures that no liquids leak out via the fine bore needle 130 as the fine bore needle 130 is surrounded and encased by the plug 210.

Referring now to FIGS. 3A and 3B, there are shown a perspective view of an alternate embodiment of the venturi inhalation device, and a cross-sectional view of an alternate embodiment of the venturi inhalation device. In the shown alternate embodiments, the venturi inhalation device comprises a housing 300 with a first open end 301 and an opposing second open end 302 defining an internal volume 310. The internal volume 310 further comprises an internal reservoir 320. In some embodiments, the internal reservoir 320 is sized to encompass the entire internal volume 310. In the shown embodiment, the internal reservoir 320 is a portion of the internal volume 310.

The internal reservoir 320 is in fluid communication with a fine bore needle 330. A distal end 331 of the fine bore needle 330 is positioned in a mouthpiece 340, wherein the mouthpiece 340 is disposed on the opposing second end 302 of the housing 300. Similar to the embodiments described above, this enables a fluid stored within the internal reservoir 320 to flow through the fine bore needle 330 and into the mouth of a user when the user simply draws a breath and inhales via utilization of the device.

The housing 300 further comprises a venturi restriction in fluid communication with the internal reservoir 320. In the shown embodiment, the venturi restriction comprises a pair of vents 350 disposed in the housing 300, wherein the pair of vents 350 are in fluid communication with the mouthpiece 340. In the shown embodiment, the vents 350 are disposed at an angle in the housing 300 such that air drawn in through the vents 350 converges together. The distal end 331 of the fine bore needle 330 is positioned in the venturi restriction, and in the shown embodiment, the distal end 331 of the fine bore needle 330 is positioned at the point through which air drawn in through the vents 350 converges.

In the embodiment shown in FIG. 3A, the fine bore needle 330 is disposed at an obtuse angle relative to a vertical plane of the internal reservoir 320. Additionally, the mouthpiece 340 is also disposed at an obtuse angle relative to a vertical plane of the internal reservoir 320. The obtuse angles utilized in the device has the optional ability to be charged by the patient prior to inhalation. In the shown embodiment, a medicament is dripped or otherwise added to the open, upright first end 301 of the housing 300, thereby filling the internal reservoir 320. In the shown embodiment, the distal end 331 of the fine bore needle 330 can be sealed via a removably securable plug 360 to prevent inadvertent flow dependent upon the bore of the needle. Thus, in the shown embodiment, the device further comprises a removably securable plug 360, wherein the plug 360 is configured to receive the distal end 331 of the fine bore needle 330. This would be a consideration for instances that have a lag time from filling to inhalation. The flow through the needle can be sufficiently slow to prevent material loss as well as the need for a pause in repeated inhalations.

Figure 3B:
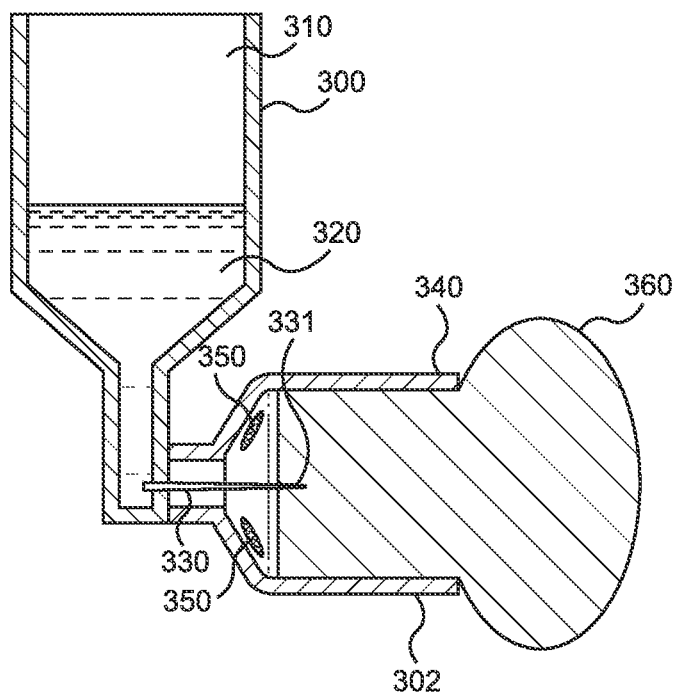

In the embodiment shown in FIG. 3B, the fine bore needle 330 is disposed at a ninety-degree angle relative to a vertical plane of the internal reservoir 320. Additionally, the mouthpiece 340 is also disposed at a ninety-degree angle relative to a vertical plane of the internal reservoir 320. In the shown embodiment, the internal volume 310 is a larger bore so that it has a smaller overall dimension. This contrasts with the pen-like straight version shown in FIGS. 1 and 2, which is long and slender. In the shown embodiment, when the device is in a horizontal position or upwardly angled, the contents of the internal reservoir 320 do not phase into a liquid layer and air layer. Thus, when the fine bore needle 330 is dispensing medication by the inhalation action of the user via the device, the contents of the internal reservoir 320 move as a plug of fluid without any phaseout interruption with air. Otherwise, the air phase would preferentially flow over the liquid and defeat the device's function. One of ordinary skill in the art will understand that the capillary bores of the needle will determine the range of viscosities that are capable of travel and dispersion. This is also dependent on the user's capacity to apply suction to the device and is intended for use by those individuals having normal or near normal lung function.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A venturi inhalation device, consisting of:
    a tube defining an internal volume;
    a fine bore needle disposed at a first end of the tube;
    the fine bore needle is in fluid communication with the internal volume;
    the tube further comprising a closed second end;
    a hollow housing sized and shaped to receive the tube in close tolerance;
    whereupon the tube being received by a first end of the housing, an air-tight seal is formed between the tube and the first end of the housing;
    the housing further comprising a venturi restriction;
    whereupon the tube being received by the first end of the housing, a distal end of the fine bore needle is positioned in the venturi restriction; and
    a mouthpiece disposed on a second end of the housing;
    wherein the housing further comprises an air inlet opening;
    wherein an air filter is disposed over an external surface of the air inlet opening;
    wherein a plug is removably secured in the mouthpiece;
    wherein the plug is a silicone elastomeric plug; and
    whereupon the plug being secured in the mouthpiece, an air-tight seal is formed between the plug and the mouthpiece.

2. The venturi inhalation device of claim 1, wherein the closed second end of the tube comprises a laminate layer.

3. The venturi inhalation device of claim 2, wherein the laminate layer is a heat-sealed laminate.

* * * * *